United States Patent
Schempp

(10) Patent No.: US 10,624,789 B2
(45) Date of Patent: Apr. 21, 2020

(54) EYE MASK WITH FACE COVER

(71) Applicant: Ali Schempp, Walnut Creek, CA (US)

(72) Inventor: Ali Schempp, Walnut Creek, CA (US)

( * ) Notice: Subject to any disclaimer, the term of this patent is extended or adjusted under 35 U.S.C. 154(b) by 191 days.

(21) Appl. No.: 15/732,460

(22) Filed: Nov. 16, 2017

(65) Prior Publication Data
US 2019/0053948 A1  Feb. 21, 2019

Related U.S. Application Data

(60) Provisional application No. 62/605,639, filed on Aug. 21, 2017.

(51) Int. Cl.
*A61F 9/04* (2006.01)
*A41D 13/11* (2006.01)
*A41D 20/00* (2006.01)
*A62B 23/00* (2006.01)
*A41D 15/00* (2006.01)
*A61M 21/00* (2006.01)
*A62B 23/02* (2006.01)

(52) U.S. Cl.
CPC ............ *A61F 9/04* (2013.01); *A41D 13/1161* (2013.01); *A41D 13/1184* (2013.01); *A41D 15/002* (2013.01); *A41D 20/00* (2013.01); *A61M 21/00* (2013.01); *A62B 23/00* (2013.01); *A62B 23/025* (2013.01); *A41D 2300/50* (2013.01); *A61M 2021/0016* (2013.01)

(58) Field of Classification Search
CPC ...... A61F 9/02; A61F 9/04; A61F 9/06; A61F 9/025; A61F 9/027; A61F 9/029; A61F 9/045; A61F 9/064; A41D 13/11; A41D 13/1161; A41D 13/1184; A41D 13/1218; A41D 15/002; A41D 20/00; A41D 2300/50; A62B 18/00; A62B 18/02; A61M 2300/50; A61M 2021/0016; A61M 21/00; A61M 23/00
USPC ............ 128/857, 858, 863; 2/173, 174, 206
See application file for complete search history.

(56) References Cited

U.S. PATENT DOCUMENTS

| 7,481,530 | B2 * | 1/2009 | Brillouet ................ G02C 11/00 2/12 |
| 2004/0074498 | A1 * | 4/2004 | Begum .............. A41D 13/1161 128/206.21 |
| 2008/0297718 | A1 * | 12/2008 | Brillouet ................ G02C 11/00 351/158 |
| 2010/0229275 | A1 * | 9/2010 | Wilson ...................... A61F 9/04 2/15 |

(Continued)

*Primary Examiner* — Anna K Kinsaul
*Assistant Examiner* — William T Kao
(74) *Attorney, Agent, or Firm* — West & Associates, A PC; Stuart J. West

(57) ABSTRACT

An eye mask with face cover panel where the eye mask is made of an inner panel and an outer panel. The face cover is stored within the space in between the two eye mask panels. A releasable strap at the bottom of the eye mask panels holds the face cover inside the mask for storage. The face cover panel is held in the storage position by a left and right spring reel assembly. Small spring biased clips hold the cords of the spring reels in place when the user pulls down on the face cover panel to use as face protection. To return to the face panel to the stored position, the user presses on the spring biased clips to cause the face cover panel to automatically lift back up into the space between the inner and outer eye mask panels.

4 Claims, 5 Drawing Sheets

(56) References Cited

U.S. PATENT DOCUMENTS

2016/0151650 A1\* 6/2016 Reese ................ A41D 13/1161
                                                    128/863
2017/0013894 A1\* 1/2017 Lee .................... A41D 13/1107

\* cited by examiner

EYE MASK WITH FACE COVER

CROSS REFERENCE TO RELATED APPLICATIONS

Not Applicable

STATEMENT REGARDING FEDERALLY SPONSORED RESEARCH OR DEVELOPMENT

Not Applicable

DESCRIPTION OF ATTACHED APPENDIX

Not Applicable

BACKGROUND OF THE INVENTION

This invention relates generally to the field of eye masks and more specifically to an eye mask with face cover. Eye masks are well known and are traditionally used when a person desires to create a darkened environment for his or her eyes while the surrounding environment is still light, for example on an airplane trip.

Eye masks have been made from a variety of relatively soft materials including fabric and Lycra covered neoprene. They generally include an elastic head strap to help hold the mask onto the user's head. In some cases, eye masks include a pocket to store a pair of ear plugs, which are commonly also needed when traveling in a noisy environment such as an airplane.

Although current eye masks perform their job efficiently, there are times when a person would like the added feature of a face cover both for privacy and for acting as an air filter to restrict airborne pollutants. An eye mask that includes a built in retractable face cover would be an ideal and novel solution.

BRIEF SUMMARY OF THE INVENTION

The primary object of the invention is to provide an eye mask that includes a built-in face cover panel that can be pulled down from a cavity within the eye mask to provide additional privacy and air filtration and can be returned to the eye mask cavity when not needed.

Another object of the invention is to provide an eye mask with built-in face cover where the face cover can be returned to the cavity within the eye mask by a mechanically assisted means.

Other objects and advantages of the present invention will become apparent from the following descriptions, taken in connection with the accompanying drawings, wherein, by way of illustration and example, an embodiment of the present invention is disclosed.

In accordance with a preferred embodiment of the invention, there is disclosed an eye mask with face cover comprising: an inner eye mask panel, an outer eye mask panel, a face cover panel, a head strap, a retaining strap, said eye mask panels and said face cover panel being flexible, said inner eye mask panel and said outer eye mask panel sewn together at their upper edge and their left and right side edges, said face cover panel being sewn at its top edge within the upper portion of the cavity formed by said inner eye mask panel and said outer eye mask panel, said retaining strap fixed to the bottom edge of said outer eye mask panel and removably adhered to said inner eye mask panel by standard means, said face cover panel capable of being stored within the said cavity and retained in said cavity by said retaining strap, and said face cover panel capable of being pulled down from said eye mask cavity thereby enabling said face cover panel to cover a person's face for the purpose of privacy or air filtration.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

Figure 1:
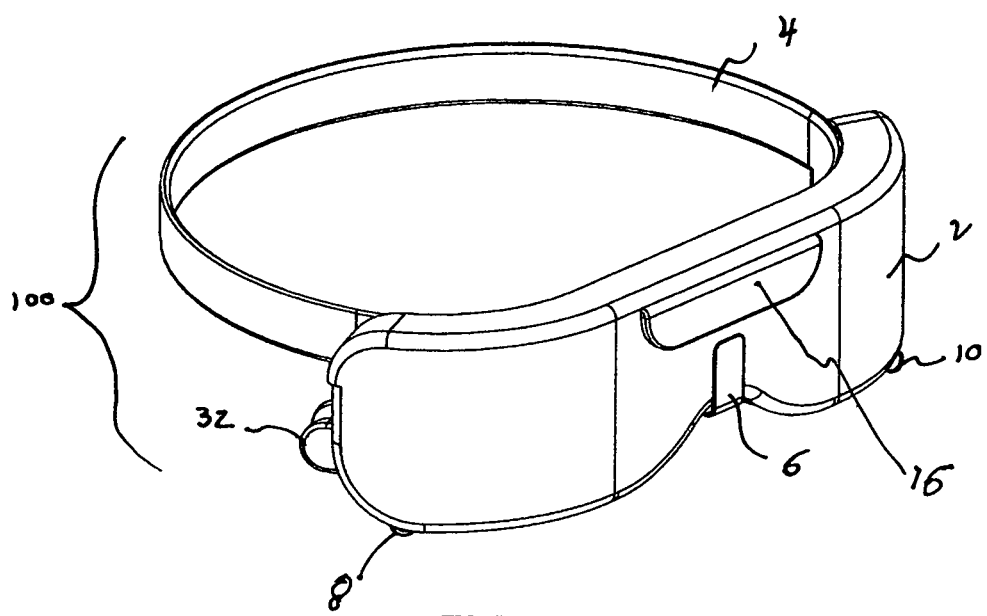
FIG. 1 is a perspective view of the invention with the face cover in the stored position.

Referring now to FIG. 1 we see a perspective view of the invention 100. The overall appearance is that of a traditional eye mask that includes an outer eye covering panel 2, and a head strap 4. The present invention 100 also includes a pouch 16 for storing ear plugs and a lower releasable strap 6 as well as pull rings 8, 10 that will be explained below.

Figure 2:
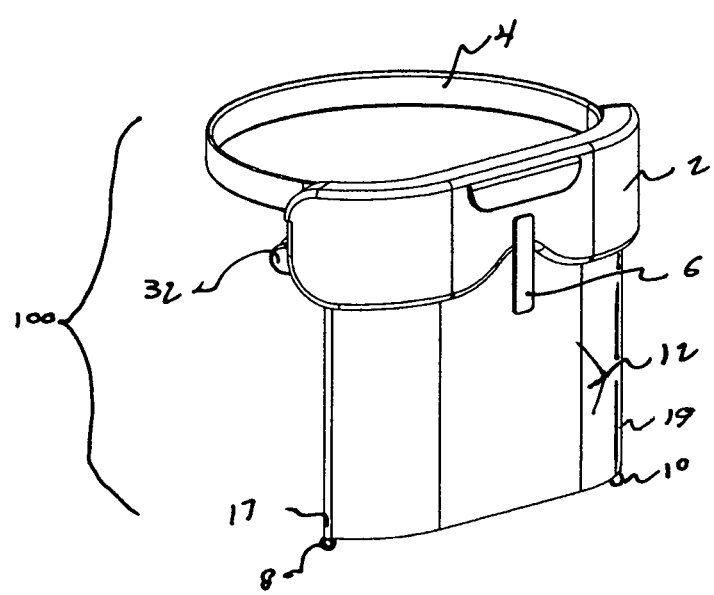
FIG. 2 is a perspective view of the invention with the face cover in the use position.

FIG. 2 is a perspective view of the invention 100 in the use position. Releasable strap 6 has been released allowing a flexible face cover panel 12 has been pulled down by rings 8, 10 and cords 17, 19 for use as a privacy panel and an air filtration device. The face cover 12 can include specific air filtration materials including activated charcoal powder and electro-statically charge fibers that are known to trap air pollutants, germs and bacteria. The face cover 12 can also include an absorbent panel that can store and release aroma therapy oil which, when smelled, has been known to help create various relaxation effects depending on the oil being used. The face cover 12 ideally is made of light weight material such as thin silk, so that the material does not disturb a woman's makeup. Additionally, the eye mask inner eye covering panel 28 may include padding that surrounds the eye socket of the wearer so that the eye mask inner eye covering panel 28 does not disturb a woman's eye makeup.

Figure 3:
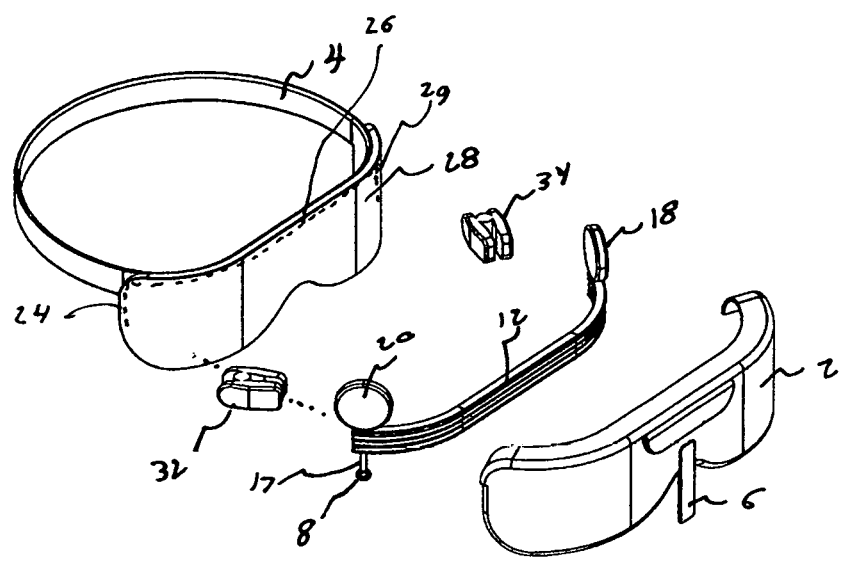
FIG. 3 is an exploded view of the invention.

FIG. 3 is an exploded view of the invention 100. The eye mask portion is comprised of an outer panel 2 and an inner panel 28. The two panels 2, 28 are sewn at their top and side edges as shown by dotted lines 26 24, 29. The lower portion of the two panels 2, 28 remain open to allow the face cover panel 12 to be pull out from the cavity between the two eye mask panels 2, 28. Left spring reel 20 and right spring reel 18 are mounted to the left and right sides of inner eye mask panel 28. The cords 40, 42 are sewn onto the left and right sides of the face cover panel 12. Pull rings 8, 10 are attached to the ends of cords 17, 19 for use to pull down the cords and attached face cover panel 12. The cords 17. 19 are held in the deployed position by spring biased clamps 32, 34. To lift the face cover panel 12 into the storage position, the user presses on the tops of clips 32, 34 which releases the cords 17, 19 and allows them to be drawn up into spring reel housings 18, 20.

Figure 4:
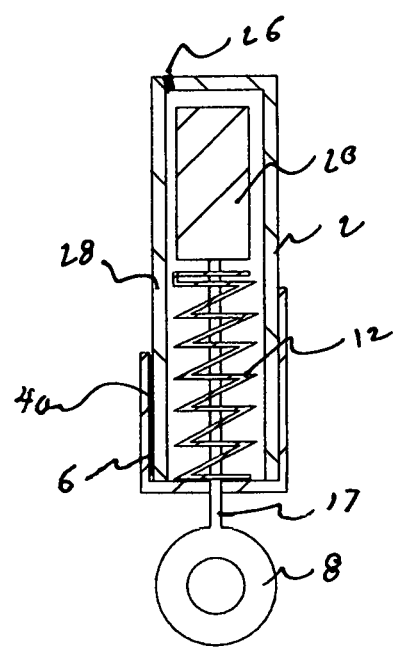
FIG. 4 is a side section view of the invention.

FIG. 4 is a side section view of the invention. outer eye mask panel 2 and inner eye mask panel 28 can be seen as sewn at top edge 26. Face cover panel 12 can be seen in its stored position within the cavity formed by the two eye mask panels 2, 28. Releasable strap 6 is in place via hook and loop fastener 40 and prevents the face cover panel 12 from exiting the cavity space when not in use.

Figure 5:
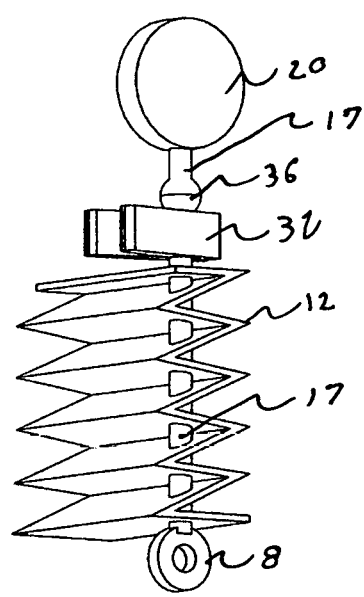
FIG. 5 is a perspective view of the spring reel assembly that is used to lift the face cover.

FIG. 5 is a detailed perspective view of the spring reel assembly including cord housing 20 and cord 17 with face cover panel 12 woven into place on the cord 17. Pull ring 8 is used for pulling the cord 17 down. Spring biased clip 32 is retaining the cord 17 in its deployed position. An enlarged portion 36 located on the cord 17 further prevents the cord 17 from retracting until the user presses down on spring biased clamp 32.

It should be noted that in one embodiment of the invention, the face cover panel 12 can simply be returned to the eye mask cavity by the user manually pushing the face cover panel 12 up into the eye mask cavity and then replacing strap 6. Additionally, other embodiments of the invention can use other mechanisms to lift the face cover panel 12, such as rolling the panel 12 up on a flexible shaft. Furthermore, the method of closing the lower portion of the eye mask panels 2, 28 can vary, including using snap fasteners and magnetic fasteners.

In another alternate embodiment, a semi rigid elongate member can be adhered to the bottom edge of the face cover panel so that the user can pull on the semi rigid elongate member to deploy the face cover panel 12 rather than pulling on the two rings 8, 10 described in the first embodiment.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. An eye mask with face cover comprising:
   an inner eye mask panel;
   an outer eye mask panel;
   a face cover panel;
   a head strap;
   a lower releasable strap;
   said eye mask panels and said face cover panel being flexible;
   said inner eye mask panel and said outer eye mask panel sewn together at their upper edge and their left and right-side edges;
   said face cover panel being sewn at its top edge within the upper portion of a cavity formed by said inner eye mask panel and said outer eye mask panel;
   said lower releasable strap fixed to the bottom edge of said outer eye mask panel and removably couplable to said inner eye mask;
   said face cover panel capable of being stored within the said cavity and retained in said cavity by said lower releasable strap;
   said face cover panel capable of being pulled down from said eye mask cavity thereby enabling said face cover panel to cover a person's face for the purpose of privacy or air filtration; and
   left and right spring reel assemblies wherein said left spring reel assembly is fixedly mounted within the left side of said eye mask cavity and said right spring reel assembly is mounted within the right side of said eye mask cavity;
   wherein cords of said spring reels are each attached to the right and left sides of said face cover panel respectively causing said face panel to automatically be lifted and stored within said eye mask cavity.

2. The eye mask with face cover panel as claimed in claim 1 wherein said left and right cords are each releasably retained by left and right spring biased clamps; wherein pushing on the tops of said spring biased clamps by the user causes said left and right cords and attached said face cover panel to retract.

3. The eye mask with face cover panel as claimed in claim 1 wherein said face cover panel includes additives that help trap air pollutants or that release pleasing aromas.

4. The eye mask with face cover panel of claim 3 wherein said left and right cords are each releasably retained by left and right spring biased clamps; wherein pushing on the tops of said spring biased clamps by the user causes said left and right cords and attached said face cover panel to retract.

* * * * *